US005324822A

United States Patent [19]
Duffy

[11] Patent Number: 5,324,822
[45] Date of Patent: Jun. 28, 1994

[54] METHOD OF ISOLATING A CA 195-LIKE IMMUNOREACTIVE ANTIGEN FROM HUMAN AMNIOTIC FLUID

[75] Inventor: Thomas H. Duffy, Santa Ana, Calif.
[73] Assignee: Ciba Corning Diagnostics Corp., Medfield, Mass.
[21] Appl. No.: 993,588
[22] Filed: Dec. 21, 1992

Related U.S. Application Data

[62] Division of Ser. No. 685,301, Apr. 12, 1991.
[51] Int. Cl.⁵ .................. C07K 1/14; C07K 15/14; A61K 35/50
[52] U.S. Cl. .................. 530/412; 530/395; 530/413; 530/414; 530/828; 424/88; 424/558; 424/582; 424/583
[58] Field of Search .............. 530/395, 412, 828, 413, 530/414, 828; 424/88, 558, 582, 583; 514/8

[56] References Cited

U.S. PATENT DOCUMENTS

| | | | |
|---|---|---|---|
| 4,229,426 | 10/1980 | Haagensen | 424/1 |
| 4,376,110 | 3/1983 | David et al. | 436/513 |
| 4,389,392 | 6/1983 | Adachi | 424/1 |
| 4,440,863 | 4/1984 | Haagensen, Jr. | 436/539 |
| 4,455,380 | 6/1984 | Adachi | 436/504 |
| 4,486,530 | 12/1984 | David et al. | 435/7 |
| 4,489,166 | 12/1984 | Joshi | 436/510 |
| 4,571,382 | 2/1986 | Adachi | 435/7 |
| 4,582,787 | 4/1986 | Frankel | 435/5 |
| 4,687,733 | 8/1987 | Trewyn et al. | 435/7 |
| 4,818,709 | 4/1989 | Primus et al. | 436/518 |

OTHER PUBLICATIONS

*Fundamental Immunology,* 1989, pp. 923-939 Schreiber, H. "Tumer Immunology".
Biegelmayer, C., et al. Tumor Biol 10:232-242 (Oct. 5, 1989) MCA, a monoclonal-antibody defined breast tumor-associated and its relation to CA 15.3.
Duffy, T. H., et al., Clinical Chemistry 35(6):1079 (Jul. 25, 1989), "Tumor markers in seminal plasma and amniotic fluid".
Gadler, H., Int. J. Cancer 25:91-94 (1980), "Distribution of tumor-associated antigen CEA and cross-reacting NCA in fetal organs".
Hyöty, M., et al., Eur. J. Surg. 158:173-179 (1992), "Tumour antigens CA 195 and CA 19-9 in pancreatic juice and serum for the diagnosis of pancreatic carcinoma".
Jacobs, I. J., et al., British J. Obstet. Gynacol. 95:1190-1194 (Nov. 1988), "The distribution of CA 125 in the reproductive tract of pregnant and non-pregnant women".
Lellé, R. J., et al., Gynecol. Obstet. Invest. 27:137-142 (1989), "Measurement of CEA, TPA, Neopterin, CA125, CA153, and CA199 in sera of pregnant women, umbilical cord blood and amniotic fluid".
Masson, P., et al., Int. J. Pancreatol. 8:333-344 (1991), "Evaluation of CEA, CA 19-9, CA-50, CA-195, and TATI with special reference to pancreatic disorders".
Wobbes, T., et al., Cancer 69(8):2036-2041 (Apr. 15, 1992), "Evaluation of seven tumor markers (CA 50, CA 19-9, CA 19-9 TruQuant, CA 72-4, CA 195, CEA and Tissue Polypeptide Antigen) in the pretreatment sear of patients with gastric cardinoma".
Bhargava, A. K. et al., Circulating CA-195 in Colorectal Cancer, 2 J. Tumor Marker Oncology (1987) 319.
Bray, K. R. et al., A Monoclonal Antibody that Detects a Tumor Associated Antigen in the Sera of Patients with Colon Cancer, 43 Federation Proceedings (1987) 1059.
Gupta, M. K. et al. CA-195: A New Sensitive Monoclonal Antibody-Defined Tumor Marker for Pancreatic Cancer, 2, J. Tumor Marker Oncology (1987) 201.
Gaur, P. K. et al., Relationship Between Cancer Associated Antigen 195 (CA-195) and CEA, 28 Proceedings of AACR (1987) 357.
Bray, K. R. et al., Serum Levels of Cancer-Associated Antigen 195, a Circulating Marker for Colon Cancer, and its Relationship to Carcinoembryonic Antigen, 2 Journal of Clinical Laboratory Analysis (1988) 187-193.
EP Search Report.

*Primary Examiner*—Christine M. Nucker
*Assistant Examiner*—T. Cunningham
*Attorney, Agent, or Firm*—Arthur S. Morgenstern; Nicholas I. Slepchuk, Jr.

[57] ABSTRACT

A method of isolation of a material with similar immunological properties to CA-195 from human amniotic fluid has been disclosed. This material can be substituted for CA-195 in many processes, for example in the preparation of analytical control materials.

16 Claims, No Drawings

METHOD OF ISOLATING A CA 195-LIKE IMMUNOREACTIVE ANTIGEN FROM HUMAN AMNIOTIC FLUID

This is a divisional of copending application Ser. No. 07/685,301 filed on Apr. 12, 1991.

SUMMARY OF THE INVENTION

A CA 195-like immunoreactive antigen has been identified in human amniotic fluid. This material appears to perform the same as and quite likely have the same composition as CA 195. This invention also relates to the isolation, and use, of the CA 195- like material.

BACKGROUND OF THE INVENTION

CA 195 is a tumor associated antigen which is identified by means of a monoclonal antibody, CC3C195 (Bray et al., 1987). Normal subjects show very low or undetectable serum CA 195 levels by the currently utilized radioimmunometric method (Gupta et al., 1987; Sundaram et al., 1987; Bhargavva et al., 1987). However, elevated levels are often found in patients with pancreatic, gastric, liver, colorectal and other gastrointestinal malignancies (Bhargava et al., 1987). Sundaram et al., (1987) found CA 195 to be superior in the identification of colon cancer to the classically utilized tumor marker CEA. Serum levels are primarily used for prognosis and progress of the disease. Although the marker shows less utility in the diagnostic phase, it is still used as an adjunct tool. Hybritech Inc. developed a radioimmunoassay for the identification of the antigen utilizing membranes from a human colon tumor. This radioimmunoassay is commercially available through Hybritech Inc. Calibrators and controls for this assay can be obtained from various malignant tissues or a human colon cancer cell line (Fukuta et al., 1987). However, human cancerous tissue is difficult to obtain, costly, and poses numerous safety problems. Obtaining the CA 195 from human cell lines requires tissue culture facilities, presents safety problems, is costly, and relatively small quantities are obtained.

This invention relates to the identification of an CA 195-like material in human amniotic fluid. This material is present in amniotic fluid in a much higher level than that in normal human serum and can be isolated without encountering the difficulties of handling the other human materials. The identification of the CA 195-like material in amniotic fluid has lead to the ability to isolate a material which is much less expensive to produce than the previous materials and methods and which appears to be as useful as the previous materials.

The invention covers not only the identification of the material but also techniques for isolation and use of the CA 195-like material.

DETAILED DESCRIPTION OF THE INVENTION

This invention covers the identification of a novel source for CA 195-like antigen, a material which has been found to perform the same immunologically, and believed to be the same composition-wise, as CA 195. This invention also relates to the isolation of, and use of, the CA 195-like material.

Human amniotic fluid was collected from human subjects and analyzed to determine the presence of the CA 195 material. To analyze the fluid a commercially available radioimmunoassay technique was used (Product CA-195-RIA, purchased from Hybritech Inc., La Jolla, Calif.), wherein a solid phase, two-site immunoradiometric assay was used. In the assay, the sample reacted with a plastic bead which was coated with an antibody directed against the CA 195 antigen and, simultaneously, with radiolabeled antibody of the same specificity. It was found that the CA 195 material was present in human amniotic fluid at a level much higher than that found in human serum. Levels in human amniotic fluid were found to range from approximately 800–1,000 U/ml, while those found in normal human serum were less than 10 U/ml. In human serum a concentration of above 10 U/ml has been associated with a cancerous state (Bhargava et al., J. Tumor Marker Oncology, 2 (1987) 319). The fact that the immunoassay detected the substance in the amniotic fluid indicated that the material was similar if not identical in immunologic properties to the authentic CA 195 antigen.

In addition, further work can be done to isolate the material from human amniotic fluid using techniques known to those with expertise in the field. These techniques include, but are not limited to, chromatographic and immunometric techniques.

Once the CA 195 material is isolated it can be utilized in a number of applications where CA 195 from malignant tissue had been used by other laboratories, namely to develop materials which could be used as controls for clinical assays for the quantitative and qualitative measurement of CA 195 in human serum.

It is further contemplated that the CA 195-like material could be used as an immunogen to develop an antibody. Polyclonal, monoclonal or other antibodies could be raised against the CA 195-like material. The technology for production of antibodies (polyclonal or monoclonal) has been well established. For production of polyclonal antibodies, the human CA 195-like material could be injected into the desired animal (usually rabbit) to produce an immunogenic response. The animal's serum would then be used as a source of antibody to CA 195. It would be especially useful to have large quantities of purified CA 195, to use as the immunogen, in order that the animals would produce only antibodies specific for CA 195 and not for extraneous proteins. For production of monoclonal antibodies, the human CA 195-like material could be injected into the desired strain of mouse (or other animal when the technology becomes established), immortal antibody secreting cell lines produced, and these cell lines screened for CA 195 recognition. Once again large quantities of purified CA 195 would cut the screening time as well as greatly increase the chances of obtaining a cell line secreting antibody specific for CA 195.

Techniques are well known by those expert in the field for producing antibodies (monoclonal, polyclonal, etc.) See, for example, Koehler, G. and Milstein, C., 256 Nature (1975) 495; and Davis, B., R. Dulbecco, H. Eisen, H. Ginsberg and W. Wood, Principles of Microbiology and Immunology, 2d., Harper & Row, New York, 1973.

The above describes the best mode contemplated by the inventor for the use of the CA 195-like material. However, it is contemplated that CA 195-like materials could be substituted for authentic CA 195 in all analytical procedures including, without limitation, radioimmunoassay, ELISA, and other analytical techniques. For example, most immunoassays for the identification of an antigen utilize either a labelled antigen or a labelled antibody. CA 195-like antigen or antibody could be labelled using various established techniques, for example, the addition of a radioactive label, an enzymatic label, a fluorescent label, a chemiluminescent label or other label which would make the material useful in an immunochemical analytical technique. These labels would serve as the reporting groups in the immunoassays. Standards or calibrators are also usually needed which contain known concentrations of the desired antigen. CA 195-like material from human amniotic fluid, or antibodies produced therefrom, could provide an inexpensive source for these constituents. It is also contemplated that human amniotic fluid might be concentrated and utilized, or perhaps even utilized without concentration, in other analytical techniques where authentic CA 195 itself might currently be used.

Either the CA 195-like material or antibody produced therefrom could be immobilized on a solid support. Numerous supports could be used, for example agarose resins (Sepharose, etc.), glass beads, etc. An immobilized antibody to CA 195 could act as a rapid and efficient purification tool to obtain pure CA 195 from crude sources. Likewise, pure antibody could be obtained utilizing immobilized CA 195-like material. These immunoaffinity chromatographic methods are well established in the literature.

The preceding illustrates examples of how immobilized ligands can be utilized but should not be construed to limit their usefulness. For example, immobilized CA 195 antibody could be used as a stripping agent to obtain CA 195 free serum.

The following examples describe various aspects of the collection, identification, purification and utilization of the CA 195-like material. However, these examples are not intended to limit the usefulness of the newly invented material or techniques for isolation or utilization thereof.

EXAMPLE 1

Human Amniotic Fluid Collection

Raw human amniotic fluid is pooled and filtered through cheesecloth (to remove particulates). The pH of the pool is adjusted to 6.8 plus or minus 0.1 with 4N HCl or 6N NaOH. The pool is then filtered through cartridges of 3.0 micron retention or less. The pool is then stored frozen at $-20°$ C.

EXAMPLE 2

Radioimmunoassay of Amniotic Fluid Samples

The required samples of amniotic fluid are thawed and assayed for the presence of CA 195 using a radioimmunoassay purchased from Hybritech Inc., La Jolla, Calif. This is a solid phase two site assay in which sample is reacted with a plastic bead which is coated with an antibody directed against the CA 195 antigen and, simultaneously, with radiolabeled antibody of the same specificity. The manufacturer's instructions are followed exactly as provided. In this assay, the bead is mixed with the samples of amniotic fluid and with radioactively labeled CA 195 antibody. The bead is then washed to remove unbound labeled antibody. The radioactivity bound to the solid phase is directly proportional to the concentration of CA 195 present in the test sample.

The kit contains I-125 labeled anti-CA 195, anti-CA 195 coated beads, CA 195 standards (0, 10, 30, 60, 90, and 120 U CA195/ml) and instructions for use.

Fifty microliters of standards or specimens are pipetted into the assigned tubes. Two hundred microliters of I-125 labeled anti-CA 195 are then pipetted into all tubes. One bead is placed into each tube. The tubes are vortexed and then put on a horizontal rotator set at 170 rpm for two hours at room temperature. The beads are then washed with 2 ml of wash solution three times and then read in a suitable well-type gamma scintillation counter.

EXAMPLE 3

Crude CA 195 Antigen

The following is an example of a procedure to manufacture crude CA 195 from human amniotic fluid: Human amniotic fluid is collected and immediately frozen for storage. When ready to use, the amniotic fluid is allowed to thaw to yield the desired quantity in weight. Every container is inspected for satisfactory physical characteristics. All equipment is inspected for cleanliness and if needed, equipment for final filtration is steam cleaned. CA 195 radioimmunoassays are run as described in Example 2. Only samples which show greater than 800 U/ml are accepted. The amniotic fluid is filtered through cheesecloth and the weight recorded. The pH of the pool is adjusted to 6.8 plus or minus 0.1 with 4N HCl or 6N NaOH. The pool is then filtered through a cartridge of at least 3.0 microns. The filtrate is then concentrated to approximately 8000 U/ml using a concentration device (e.g., an Amicon Stirred Cell Model 8400, utilizing a YM 10 membrane) with a molecular cut off less than 10,000 daltons. The concentrate is then dialyzed against $10 \times 10\text{-}3M$ potassium phosphate buffer pH 6.9 (100 fold) overnight (5° C.). The dialysate is then filtered into a steam cleaned tank through a 0.45 micron filter and filled into clean bottles at the desired levels. The product is either stored frozen at $-20°$ C. or lyophilized according to Example 4.

EXAMPLE 4

Lyophilization Procedures

Industrial vacuum dryers (Hull Corporation, Hatboro, Pa., model 651VC36F40) can be utilized for the lyophilization process, using the following procedure: The shelf temperature is lowered to a minimum of $-29°$ C. prior to loading samples. The product is then loaded and once all product temperatures have reached $-29°$ C. or below, the shelf temperature is set to $+5°$ C. The temperature is maintained at $+5°$ C. until all product reaches $-1°$ C. The temperature is then increased to $+16°$ C. where it is maintained until all product reaches $+10°$ C. At this point, the temperature is increased to $+27°$ C. and maintained until all product temperatures have reached $+21°$ C. The shelf temperature is then increased to $+43°$ C. and maintained until all product temperatures reach $+38°$ C. When the product temperature reaches $+38°$ C. on all product readings, then an additional 12 hours is required. After the dryer cycle is completed then dryers are vented and product is unloaded.

EXAMPLE 5

Standard Grade CA 195

The following is a procedure to manufacture partially purified CA 195 from human amniotic fluid: The procedure for crude CA 195 as described in Example 3 is followed through the concentration step. A Sephadex G-200 column is then prepared and the void volume determined using a blue dextran solution. The concentrate is then applied to the Sephadex G-200 sizing column. Tubes are collected which corresponded to the void volume (based upon the pre-calibration) and assayed for CA 195 activity using the radioimmunoassay described in Example 2. The CA 195 positive peak is pooled and concentrated to approximately 8,000 U/ml using a molecular weight cut off less then 10,000 and filtered through a 0.45 micron filter. The product is then filled into bottles at the desired levels and stored frozen or lyophilized as described in Example 4.

EXAMPLE 6

Tumor Marker Control Containing CA 195

The following is a procedure to manufacture a tumor marker control containing CA 195 in a human serum base: Sufficient containers of human serum to yield desired weight are allowed to thaw. Total protein is between 5.0 and 6.0 g/dl. The human serum should not show any visible signs of bacterial contamination. Serum and unpurified stock solutions are then tested for endogenous levels of all constituents stated below. The pH of the serum is adjusted to 6.1 (using 4N hydrochloric acid) and stirred until the pH reaches approximately 6.8. The solution is made $1.5 \times 10^{-2}M$ in Hepes buffer and the pH adjusted to 6.8–7.0. 0.1 to 0.5% of Celite is added to the pooled serum, mixed, and filtered through pads of at least 0.5 microns. The following constituents are then added to the desired levels while mixing the pool at a medium speed: alphafeto protein, carcinoembryonic antigen, CA 125, CA 19-9, CA 50, CA15-3, ferritin, beta-hCG, immunoreactive elastase, prostatic acid phosphatase, tissue polypeptide antigen, and CA 195 (from human amniotic fluid). The pool is filtered through a 0.45 micron filter and filled at 5.2 ml per vial. The product is then lyophilized as described in Example 4.

What is claimed is:

1. A metod of isolation of a material with similar immunological properties to CA 195 from human amniotic fluid comprising:
   a) selecting human amniotic fluid samples containing material with similar immunological properties to CA-195, and
   b) purifying or separating the material with similar immunological properties to CA-195 away from other components of amniotic fluid.

2. The method of claim 1 wherein the selection comprises the use of immunometric procedures.

3. The method of claim 1 wherein the purifying or separating steps involve chromatographic or imunoaffinity techniques.

4. The method of claim 1 wherein the purifying or separating steps result in the preparation of material which is useful as an immunological standard, calibrator or control.

5. The method of claim 1 wherein the purifying or separating steps involve the use of chromatographic techniques.

6. The metod of claim 5 wherein the chromatographic techniques are selected from gel filtration or immunoaffinity chromatography.

7. The method of claim 4 wherein the preparation involves increasing the concentration of material with similar immunological properties to CA-195.

8. the method of claim 7 wherein increasing the concentration involves the use of lyophilization.

9. The method of claim 7 wherein increasing the concentration involves the use of membrane filtration.

10. The method of claim 2 wherein the immunometric procedures are used to select those fractions of amniotic fluid which have sufficiently high concentration of the material similar in immunological properties to CA 195.

11. The method of claim 10 in which the fractions of amniotic fluid have a concentration of material similar in immunologial properties to CA 195 of greater than 800 U/ml.

12. A method of isolation of a material similar in immunological properties to CA 195 from human amiotic fluid comprising:
   a) selection of appropriate human amniotic fluid samples by the use of immunometric procedures;
   b) separation of such material by the use of column chromatography techniques; and
   c) increasing the concentration of such material by the use of lyophilization.

13. The method of claim 1 wherein the purifying or separating steps result in the preparation of an immunogen which is useful for preparign an antibody which recognizes the immunological determinant of CA-195.

14. The method of claim 1, wherein the purified or isolated material with similar immunological properties to CA-195 is concentrated above the concentration found in human amniotic fluid.

15. A method of using human amniotic fluid to isolate a material with similar immunological properties to CA-195, said method comprising the steps of:
   a) collecting human amniotic fluid,
   b) assaying said amniotic fluid for the presence of material with similar immunological properties to CA-195,
   c) selecting the samples of amniotic fluid with similar immunological properties to CA-195, and
   d) isolating the material with similar immunological properties to CA-195 away from other components of said amniotic fluid.

16. The method of claim 15 wherein the material with similar immunological properties to CA-195 is concentrated above the levels found in human amniotic fluid.

* * * * *